United States Patent
Uchida et al.

(10) Patent No.: US 6,849,759 B1
(45) Date of Patent: Feb. 1, 2005

(54) PROCESS FOR PRODUCING ESTERS (75) Inventors: Hiroshi Uchida, Oita (JP); Tomoyoshi Higashi, Oita (JP); Etsuko Kadowaki, Oita (JP); Takashige Miyanari, Oita (JP); Wataru Oguchi, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/719,985
(22) PCT Filed: Oct. 24, 2000
(86) PCT No.: PCT/JP00/07443
§ 371 (c)(1),
(2), (4) Date: Dec. 19, 2000
(87) PCT Pub. No.: WO01/30738
PCT Pub. Date: May 3, 2001

Related U.S. Application Data
(60) Provisional application No. 60/192,880, filed on Mar. 29, 2000.

(30) Foreign Application Priority Data

Oct. 25, 1999 (JP) .......................................... 11-301780
Feb. 25, 2000 (JP) .......................................... 2000-49627

(51) Int. Cl.$^7$ ............................................ C07C 67/04
(52) U.S. Cl. ........................................................ 560/247
(58) Field of Search ................................. 560/231, 247

(56) References Cited

U.S. PATENT DOCUMENTS

| 5,189,201 A | 2/1993 | Sano et al. |
| 5,861,530 A | * 1/1999 | Atkins et al. |
| 6,187,949 B1 | * 2/2001 | Froom et al. |

FOREIGN PATENT DOCUMENTS

| CN | 1232019 A | 10/1999 | |
| EP | 0 562 139 A1 | 9/1993 | ........... C07C/67/04 |
| EP | 0 757 027 A1 | 2/1997 | ........... C07C/67/04 |
| EP | 0936210 A1 | 8/1999 | |

* cited by examiner

Primary Examiner—Johann Richter
Assistant Examiner—Paul A. Zucker
(74) Attorney, Agent, or Firm—Sughrue Mion, PLLC (57) ABSTRACT

A process for producing an ester comprising reacting a carboxylic acid and ethylene in the presence of an acid catalyst in a vapor phase, wherein the concentration of olefin having 3 or more carbon atoms in the starting materials is controlled to 10,000 ppm or less in terms of the molar ratio to the total of the olefin and ethylene. The deterioration of the catalyst can be remarkably prevented from proceeding and a continuous and stable operation can be performed for a long time.

30 Claims, 3 Drawing Sheets

PROCESS FOR PRODUCING ESTERS

CROSS-REFERENCE TO RELATED APPLICATIONS

This application is an application filed under 35 U.S.C. §111(a) claiming benefit pursuant to 35 U.S.C. §119(e)(1) of the filing date of the Provisional Application No. 60/192,880 filed Mar. 29, 2000, pursuant to 35 U.S.C. §111(b).

TECHNICAL FIELD

The present invention relates to a process for producing an ester by reacting an ethylene and a carboxylic acid.

BACKGROUND ART

It is well known that a lower olefin and a lower aliphatic carboxylic acid react in the presence of an acid catalyst to provide the corresponding ester. It is also known that in this reaction, a heteropolyacid and/or heteopolyacid salt effectively act as a catalyst. Specific examples of these conventional techniques include those described, for example, in Japanese Unexamined Patent Publications No. 4-139148, No. 4-139149, No. 5-65248, No. 5-163200, No. 5-170699, No. 5-255185, No. 5-294894, No. 6-72951 and No. 9-118647. Thus, the development of catalysts having high initial activities is proceeding.

However, in industrial production processes, impurities derived from the starting materials or by-products produced during the reaction cause deterioration of the catalyst and in turn the reaction yield disadvantageously decreases. Particularly, in the process having a circulation system, if a reaction is continuously performed for a long time, various impurities or byproducts accumulate in the system and due to the effect thereof, for example, a vicious circle arises such that the catalyst deteriorates and the side reaction is further accelerated.

DISCLOSURE OF INVENTION

It is an object of the present invention to provide a process for producing an ester by esterifying a carboxylic acid with ethylene in a vapor phase, where the operation can be continuously and stably performed for a long period of time.

In particular, the object of the present invention is to provide the above-described process for producing an ester where, in a process having a circulation system, the impurities derived from the starting materials or the compounds derived from the by-products produced by a side reaction are reduced to a low concentration with respect to the starting materials, so that the catalyst can be prevented from deteriorating and, in turn, the operation can be continuously and stably performed for a long period of time.

The present inventors have made extensive studies to investigate a process for producing an ester, by reacting ethylene and a carboxylic acid, in which deterioration of the catalyst hardly occurs and the operation can be continuously and stably performed over a long period of time.

As a result, it has been found that, in a process for producing an ester by esterifying a carboxylic acid and an ethylene using an acid catalyst in a vapor phase, when the concentration of olefin having 3 or more carbon atoms in the starting materials is controlled to 10,000 ppm or less in terms of the molar ratio to the total of the olefin and ethylene, the deterioration of the catalyst can be remarkably prevented from proceeding and in turn, a continuous and stable operation can be performed for a long time.

It has also been found that, in the process for producing an ester by esterifying a carboxylic acid and ethylene using an acid catalyst in a vapor phase, when the concentration of olefin equivalent in the starting materials is controlled to 50,000 ppm or less in terms of the molar ratio to the total of the olefin equivalent and ethylene, the deterioration of the catalyst can be remarkably prevented from proceeding and a continuous and stable operation can be performed for a long time, as in the above-mentioned process.

BEST MODE FOR CARRYING OUT THE INVENTION

The present invention is described in detail below.

The term "olefin having 3 or more carbon atoms" as used herein generally refers to one or more olefins except for ethylene. Specific examples thereof include linear terminal olefins having 3 or more carbon atoms, such as propylene, 1-butene, 2-butene, isobutene, 1-hexene and 2-octene, internal olefins, branched terminal olefins, branched internal olefins, and cyclic olefins having 3 or more carbon atoms, such as cyclopentene and cyclohexene.

Among these, so-called ethylene oligomers derived from an ethylene and produced by the side reaction which may occur under the esterification reaction conditions, such as 1-butene, cis-2-butene, trans-2-butene, 2-methyl-2-pentene and 3-methyl-2-pentene, have a possibility of causing a problem. Of course, the olefins are not limited thereto.

The term "olefin equivalent" as used herein refers to one or more compounds which can produce the olefin having 3 or more carbon atoms under the esterification reaction conditions. Specific examples thereof include hydrates of olefins having 3 or more carbon atoms, ether compounds produced by the reaction of the hydrate with ethylene or an olefin having 3 or more carbon atoms, and carboxylic acid esters produced by the reaction of a carboxylic acid with an olefin having 3 or more carbon atoms. However, the olefin equivalent is not limited thereto and all compounds are included as long as they are compounds capable of producing an olefin having 3 or more carbon atoms under the esterification reaction conditions.

Specific examples of the olefin equivalent include the following compounds.

Examples of the hydrate of an olefin having 3 or more carbon atoms include isopropanol, n-butyl alcohol, sec-butyl alcohol, t-butyl alcohol and 2-hexanol.

Examples of the ether compound produced by the reaction of a hydrate of an olefin having 3 or more carbon atoms with ethylene or an olefin having 3 or more carbon atoms include ethyl isopropyl ether, ethyl sec-butyl ether, ethyl t-butyl ether, di-sec-butyl ether, di-n-butyl ether and ethyl cyclohexyl ether.

Examples of the carboxylic acid ester produced by the reaction of a carboxylic acid with an olefin having 3 or more carbon atoms include isopropyl acetate, sec-butyl acetate, sec-butyl propionate, t-butyl acetate and cyclohexyl acetate.

These compounds, namely, hydrates of olefins, ether compounds and carboxylic acid esters, are the specific examples of the equivalent of an olefin. However, needless to say, the specific examples of the olefin equivalent is not limited thereto.

The olefin equivalent also includes those produced in the reaction system as well as those contained in the starting materials newly fed to the reaction system.

Particularly, in performing the process for producing an ester by the esterification reaction of a carboxylic acid and ethylene using an acid catalyst in a vapor phase, when water is present in the system, there is a possibility that a hydrate may be produced by the hydration of ethylene and also an ether compound or a carboxylic acid ester is further produced from the hydrate. Furthermore, when a circulation system for the unreacted raw materials is integrated into the production process of an ester so as to improve the yield or the like, the hydrate, the ether compound and the carboxylic acid ester produced in the reaction system may disadvantageously mingle with the unreacted starting materials. In this document, the "olefin equivalent" as used herein includes the hydrates, ether compounds and carboxylic acid esters produced in the reaction system by the esterification reaction.

In the process for producing an ester according to the present invention, the concentration of olefin having 3 or more carbon atoms in the starting materials is controlled to 10,000 ppm or less in terms of the molar ratio to the total of the olefin and ethylene, which is effective in reducing the deterioration rate of the catalyst and in turn continuously and stably performing the operation for a long period of time.

The terms "the concentration of olefin having 3 or more carbon atoms in the starting materials" and "the concentration of olefin equivalent in the starting materials" each refers to a concentration immediately before the inlet of an reactor for performing the esterification reaction.

Figure 1:
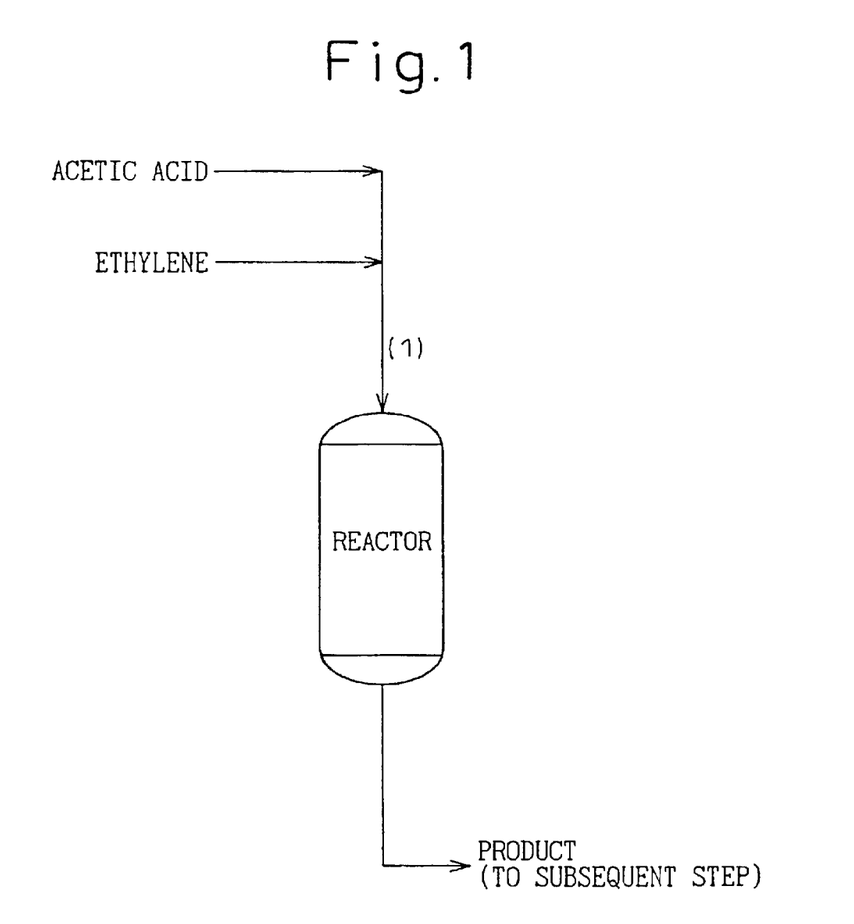
FIG. 1 is a schematic view showing a one-path process according to the invention having no circulation step, wherein acetic acid is used as a carboxylic acid.
Figure 2:
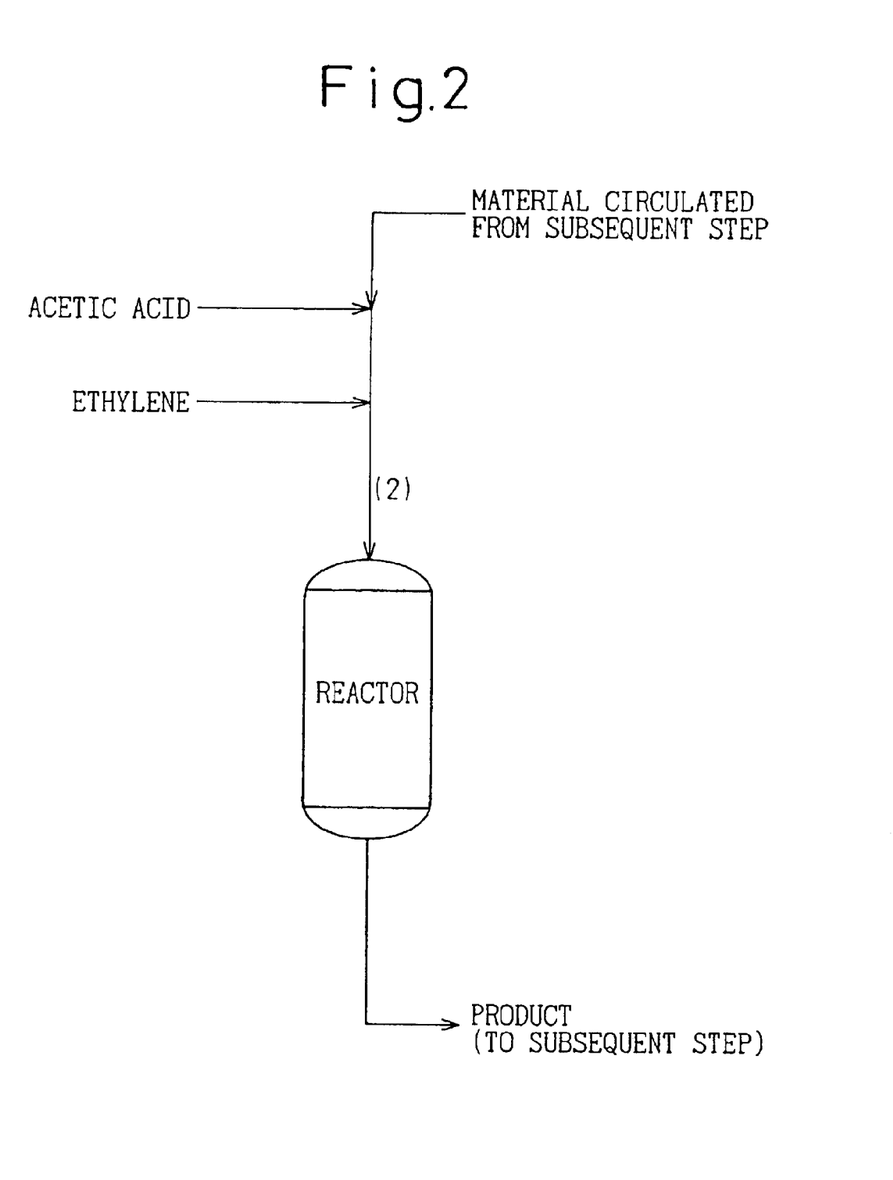
FIG. 2 is a schematic view showing a process according to the invention having a circulation step from subsequent step, wherein acetic acid is used as a carboxylic acid.

For example, specifically, in the case where the reaction is performed in the one-path process having no circulation step as shown in FIG. 1, the concentration immediately before the inlet of a reactor indicated by (1) applies. In the process having a circulation step from a subsequent step as shown in FIG. 2, the concentration immediately before the inlet of a reactor indicated by (2) applies. Needless to say, the present invention is by no means limited to these exemplified processes.

Accordingly, the term "starting materials" as used herein of course includes those obtained by recovering unreacted starting materials, through a subsequent step such as separation of the objective compound, after the reaction and supplied to the reactor via a circulation system, in addition to ethylene and acetic acid newly fed to the reaction system.

The position (1) in the process shown in FIG. 1 and the position (2) in the process shown in FIG. 2 are both kept at a temperature equal to or higher than the reaction temperature in the reactor. Accordingly, to measure the concentration at such a position, the sampling must be particularly designed.

In particular, some olefin equivalents are readily condensed when cooled to room temperature and, therefore, to avoid measurement errors due to the effect thereof, the sampling must be designed, for example, to separate the condensed components from the non-condensed components by cooling them using an ice trap or the like and analyze respective components.

If the concentration of olefin having 3 or more carbon atoms in the starting materials exceeds 10,000 ppm in terms of the molar ratio to the total of the olefin and ethylene, the catalytic activity decreases at an extremely high rate and, as a result, the catalyst life is greatly shortened. This is thought to occur because the above-described olefin reacts with ethylene on the catalyst to produce cokes and the active sites of the catalyst are covered by the cokes to cause the deactivation.

Accordingly, the concentration of olefin having 3 or more carbon atoms in the starting materials is preferably as low as possible. These olefins cannot be completely removed with ease, but the concentration is preferably 5,000 ppm or less, more preferably 1,000 ppm or less.

The method for controlling the concentration of olefin having 3 or more carbon atoms in the starting materials to 10,000. ppm or less in terms of the molar ratio to the total of the olefin and ethylene is not particularly limited. Commonly known separation techniques may be used.

As an example, fundamentally, ethylene used as a starting material should of course be refined to reduce the contents of these compounds as much as possible.

The olefin having 3 or more carbon atoms produced by the side reaction within the reaction system, which becomes a problem when a circulation system is integrated, can be separated from the ethylene by a method of allowing an appropriate solvent to absorb the main products exclusive of the ethylene, the starting materials and the by-products in the reaction gas discharged from the reactor. Also, the raw material gas may be separated from ethylene by high-pressure or low-temperature distillation or by using a separation membrane or the like. Other than these specific examples, any method may be used as long as it is a method capable of controlling the concentration of the olefin having 3 or more carbon atoms circulated and guided to the reactor to 10,000 ppm or less in terms of the molar ratio to the total of the olefin and ethylene.

If the concentration of olefin equivalent in the starting materials exceeds 50,000 ppm in terms of the molar ratio to the total of the olefin equivalent and ethylene, similarly to the case where the concentration of olefin having 3 or more carbon atoms exceeds 10,000 ppm in terms of the molar ratio to the total of the olefin and ethylene, the catalytic activity decreases at an extremely high rate and, as a result, the catalyst life is greatly shortened.

Although it may slightly differ depending on the individual olefin equivalents, the olefin equivalent generally exhibits an activity of deteriorating the catalyst on the same level as the olefin having 3 or more carbon atoms when the concentration thereof is about 5 times higher. This difference is considered to result from the fact that the olefin equivalent produces an olefin after being decomposed on the catalyst and, therefore, the effect on the deactivation is low even if the concentration is higher than that of the olefin.

However, similarly to the olefin having 3 or more carbon atoms, the concentration of the olefin equivalent is preferably as low as possible. Although complete removal of the olefin equivalent may not be attained with ease, the concentration thereof is preferably 25,000 ppm or less, more preferably 5000 ppm or less.

The method for controlling the concentration of olefin equivalent in the starting materials to 50,000 ppm or less in terms of a molar ratio to the total of the olefin equivalent and ethylene is not particularly limited. Similarly to the olefin having 3 or more carbon atoms, commonly known separation techniques may be used for the olefin equivalent.

When the olefin having 3 or more carbon atoms and the olefin equivalent are present together, an interaction therebetween is not particularly observed. Roughly, the sum of one-fifth the concentration of all olefin equivalents and the concentration of olefin having 3 or more carbon atoms in the starting materials is preferably 10,000 ppm or less in terms of the molar ratio to the total of the olefin and olefin equivalent and ethylene.

Needless to say, similarly to their individual concentrations, the concentration here is also preferably as low as possible and, specifically, it is preferably 5,000 ppm or less, more preferably 1,000 ppm or less.

The method for measuring the concentration of the olefin having 3 or more carbon atoms or the olefin equivalent is not particularly limited and any method may be used as long as it is a method commonly used for measuring the concentration. Specific examples of the measuring method include a method of placing a cell in a part of the apparatus and spectro-optically measuring the concentration using an appropriate wavelength, and a method of sampling a part of the starting material and analyzing it by gas chromatography. However, the present invention is by no means limited thereto.

The optimal measuring method varies depending on the properties of the object to be measured or the environment of the measurement, but a method which is free of any effect from other components is favored with good quantitation and reproduction, is low in measuring threshold value, and is simple and inexpensive, is preferred.

The carboxylic acid for use as a reaction starting material in the present invention is a lower aliphatic carboxylic acid having from 1 to 4 carbon atoms. Preferred are formic acid, acetic acid, acrylic acid, propionic acid and methacrylic acid, and more preferred are acetic acid and acrylic acid.

The acid catalyst for use in the present invention is a compound widely used as an acid catalyst such as ion-exchange resin, mineral acid, heteropolyacid, zeolite and composite metal oxide. Preferred are a heteropolyacid and a heteropolyacid salt. A heteropolyacid is a compound consisting of a center element and peripheral elements to which oxygen is bonded.

The center element is usually silicon or phosphorus but not limited thereto and the center element may be any one selected from the elements belonging to Groups 1 to 17 of the Periodic Table. The Periodic Table as used herein indicates the Periodic Table provided in *Muki Kagaku Meimeiho, Kaitei-Ban (Nomenclature in Inorganic Chemistry, Revised)*, Kokusai Junsei Oyobi Oyo Kagaku Rengo (1989).

Specific examples of the center element include cupric ion; divalent beryllium, zinc, cobalt and nickel ions; trivalent boron, aluminum, gallium, iron, cerium, arsenic, antimony, phosphorus, bismuth, chromium and rhodium ions; tetravalent silicon, germanium, tin, titanium, zirconium, vanadium, sulfur, tellurium, manganese, nickel, platinum, thorium, hafnium, cerium ions and other rare earth ions; pentavalent phosphorus, arsenic, vanadium and antimony ions; hexavalent tellurium ion; and heptavalent iodide ion, but the present invention is by no means limited thereto.

Specific examples of the peripheral element include tungsten, molybdenum, vanadium, niobium and tantalum, but the present invention is not limited thereto.

These heteropolyacids are also known, e.g., as "polyoxoanion", "polyoxometallate" or "metal oxide cluster". The structures of some of the well known anions are known, for example, as Keggin, Wells-Dawson or Anderson-Evans-Perloff structures. Heteropolyacids usually have a high molecular weight, for example, a molecular weight, e.g., in the range of 700 to 8,500 and include dimeric complexes.

The heteropolyacid salt is not particularly limited as long as it is a metal salt or onium salt resulting from substituting a part or all of the hydrogen atoms of the heteropolyacid.

Specific examples thereof include metal salts, e.g., such as of lithium, sodium, potassium, cesium, magnesium, barium, copper, gold and gallium, and onium salts such as of ammonia, but the present invention is not limited thereto.

Particularly when the heteropolyacid is in a free acid form or in a certain salt form, the heteropolyacid has a relatively high solubility in polar solvents such as water or other oxygenated solvents, and the solubility can be controlled by selecting the appropriate counter ions.

Examples of the heteropolyacid which can be particularly preferably used as a catalyst in the present invention include:

| | |
|---|---|
| Tungstosilicic acid | $H_4[SiW_{12}O_{40}]\cdot xH_2O$ |
| Tungstophosphoric acid | $H_3[PW_{12}O_{40}]\cdot xH_2O$ |
| Molybdophosphoric acid | $H_3[PMO_{12}O_{40}]\cdot xH_2O$ |
| Molybdosilicic acid | $H_4[SiMo_{12}O_{40}]\cdot xH_2O$ |
| Vanadotungstosilicic acid | $H_{4+n}[SiV_nW_{12-n}O_{40}]\cdot xH_2O$ |
| Vanadotungstophosphoric acid | $H_{3+n}[PV_nW_{12-n}O_{40}]\cdot xH_2O$ |
| Vanadomolybdophosphoric acid | $H_{3+n}[PV_nMo_{12-n}O_{40}]\cdot xH_2O$ |
| Molybdotungstosilicic acid | $H_{4+n}[SiMo_nW_{12-n}O_{40}]\cdot xH_2O$ |
| Molybdotungstophosphoric acid | $H_{3+n}[PV_nW_{12-n}O_{40}]\cdot xH_2O$ | wherein n is an integer of 1 to 11 and x is an integer of at least 1.

Particularly preferred examples of the heteropolyacid salt include lithium salts, sodium salts, potassium salts, cesium salts, magnesium salts, barium salts, copper salts, gold salts, gallium salts and ammonium salts of the above-described heteropolyacids which are particularly preferred.

The acid catalyst may be supported on a support. In this case, the acid catalyst content is preferably from 10 to 200 mass %, more preferably from 50 to 150 mass %, based on the entire mass of the support.

If the acid catalyst content is less than 10 mass %, the content of active components in the catalyst may excessively be lower and the activity per the catalyst unit mass may disadvantageously decrease.

If the content of the acid catalyst exceeds 200 mass %, the effective surface area may decrease and, as a result, the effect owing to the increase in the supported amount may not be brought out and at the same time, coking is disadvantageously liable to occur to greatly shorten the catalyst life.

The substance which can be used as a support for the acid catalyst of the present invention is not particularly limited and those capable of providing, when prepared as a catalyst by carrying the acid catalyst, a catalyst having a specific surface area of from 65 to 350 m²/g, as measured by BET method, is preferred.

The shape of the substance which can be used as a support for the catalyst of the present invention is not particularly limited and, specifically, a powder, spheres, pellets and any other forms may be used. Specific examples thereof include silica, diatomaceous earth, montmorillonite, titania, activated carbon, alumina and silica-alumina, but the present invention is not limited thereto.

The support is preferably a support comprising a siliceous main component and having a spherical or pellet shape, more preferably a silica having a purity of 95 mass % or more based on the entire mass of the support.

The average diameter thereof is preferably from 2 to 10 mm for use in a fixed bed system and from powder to 5 mm for use in a fluid bed system, though it varies depending on the reaction form.

The acid catalyst for use in the present invention can be produced by any desired method. For example, a process for preparing a heteropolyacid and/or heteropolyacid salt catalyst is described below, which comprises first and second steps.

First Step:

A step for obtaining a solution or suspension of a heteropolyacid and/or a heteropolyacid salt.

Second Step:

A step for supporting the solution or suspension obtained in the first step on a support.

The solvent which can be used in the first step is not particularly limited as long as it can uniformly dissolve or suspend the desired heteropolyacid and/or heteropolyacid salt, and water, an organic solvent or a mixture thereof may be used. Preferred examples thereof include water, alcohols and carboxylic acids, but the present invention is not limited thereto.

The method for dissolving or suspending a heteropolyacid and/or a heteropolyacid salt in the solvent is not particularly limited and any method may be used as long as it can uniformly dissolve or suspend a desired heteropolyacid and/or heteropolyacid salt.

For example, in the case of a heteropolyacid, namely, a free acid, if it can dissolve, the heteropolyacid may be dissolved as it is. Even when the heteropolyacid cannot completely dissolve, if the heteropolyacid can be uniformly suspended by forming it into fine powder, the heteropolyacid may be suspended as such. In the case of a heteropolyacid salt, a method of dissolving a heteropolyacid and a starting material salt for a neutralizing element together or separately and then mixing them to prepare a uniform solution or suspension may be used. Furthermore, in the case of a compound which is in the state of a heteropolyacid salt, a uniform solution or suspension may be obtained in the same manner as in the heteropolyacid.

The optimal volume of the solution or suspension varies depending on the supporting method in the second step and the support used but this is not particularly limited.

The second step is a step for supporting a solution or suspension of a heteropolyacid and/or a heteropolyacid salt obtained in the first step on a support to obtain a catalyst for use in the manufacture of a lower aliphatic The method for bearing the solution or suspension of a heteropolyacid and/or a heteropolyacid salt on a support is not particularly limited and a known method may be used.

For example, the catalyst may be prepared by dissolving or suspending a heteropolyacid and/or a heteropolyacid salt in a solvent so as to form a solution or suspension corresponding to the liquid absorption amount of the support and impregnating a support with the solution or suspension.

The catalyst may also be prepared by using an excess solution or suspension, impregnating it into a support while moderately moving the support in the solution or suspension of a heteropolyacid and/or a heteropolyacid salt and then removing the excess acid through filtration.

The wet catalyst obtained as such is preferably dried by placing it in a heating oven for a few hours. Thereafter, the catalyst is cooled to the ambient temperature in a desiccator. The drying temperature is not particularly limited but if it exceeds about 400° C., the skeleton of the heteropolyacid may be disadvantageously destroyed. The drying temperature is preferably from 80 to 350° C.

Industrially, the catalyst may be continuously dried using a dryer such as through-flow rotary dryer, continuous fluidized bed dryer or continuous hot air carrier type dryer.

The amount of the heteropolyacid and/or heteropoly-acid salt supported can be calculated simply by subtracting the mass of the support used from the dry mass of the catalyst prepared. A more exact amount may be measured by chemical analysis such as ICP (inductively coupled plasma emission spectrometry).

In practicing the process for producing an ester of the present invention, the ratio between ethylene and the carboxylic acid used is preferably such that ethylene is used in an equimolar amount or excess molar amount to the carboxylic acid. The ratio of ethylene:carboxylic acid is preferably, as a molar ratio, from 1:1 to 30:1, more preferably from 3:1 to 20:1, still more preferably from 5:1 to 15:1.

In the process of the present invention, the vapor phase reaction may be performed in either a fixed bed system or a fluidized bed system. The shape of the support may also be selected from those formed into a size of from powder to a few mm in diameter according to the system of the practice.

In the process of the present invention, a slight amount of water is preferably mixed in the starting materials from the standpoint of the catalyst life. However, if an excessively large amount of water is added, by-products such as alcohol and ether may disadvantageously increase. In general, the amount of water is preferably from 1 to 15 mol %, more preferably from 2 to 8 mol %, in the entire amount of the olefin and carboxylic acid used.

The reaction temperature and pressure must be in the range capable of keeping the supply medium in a gaseous form and varies depending on the starting materials used. In general, the reaction temperature is preferably from 120 to 250° C., more preferably from 140 to 220° C.

The pressure is preferably from atmospheric pressure to 3 MPa, more preferably from atmospheric pressure to 2 MPa.

With respect to the space velocity (GHSV) of the raw materials, these preferably pass through the catalyst layer at a GHSV of from 100 to 7,000/hr, more preferably from 300 to 3,000/hr.

The present invention is further illustrated below by referring to the examples and reference examples. However, these examples are only for describing the embodiments of the present invention, and the present invention should not be construed as being limited thereto.

Analysis of Reaction Gas

In Examples 1 to 12 and Comparative Examples 1 to 7 which are examples of the one-path process having no recycle system, the starting material composition fed to the reactor was used as the inlet gas concentration.

In Examples 13 to 15 and Comparative Example 8 which are examples of the process having a recycle system, for a gas at the inlet of the reactor, when a predetermined time was passed after the initiation of the reaction, a part of the gas was sampled by a three-way valve and cooled and the concentrated solution collected was recovered in the whole amount and analyzed by gas chromatography. With respect to the effluent gas remaining uncondensed, the flow rate of the gas at the outlet discharged within the sampling time was measured and a part of the gas was sampled and analyzed on the composition by gas chromatography on the other hand, for a gas at the outlet, the whole amount of the gas was cooled and the concentrated reaction solution collected was recovered in the whole amount and analyzed by gas chromatography. With respect to the effluent gas remaining uncondensed, the flow rate of the gas at the outlet discharged within the sampling time was measured and a part of the gas was sampled and analyzed on the composition by gas chromatography. The analysis conditions are shown below.

Conditions for Analysis of Uncondensed Gas

An absolute calibration curve method was used for the analysis. The analysis was performed under the following conditions by sampling 50 ml of the effluent gas and allowing the whole amount thereof to flow into a 1 ml-volume gas sampler attached to the gas chromatograph.

1. Ether, Carboxylic Acid Ester, Alcohol, Trace By-Products

Gas chromatography:
   gas chromatograph (GC-14B, manufactured by Shimadzu Corporation) with a gas sampler (MGS-4, measuring tube: 1 ml) for Shimadzu gas chromatograph Column:
   packed column SPAN80 15% Shinchrom A, 60 to 80 mesh (length: 5 m)

Carrier gas:
   nitrogen (flow rate: 25 ml/min)

Temperature conditions:
   constant temperature conditions where the detector and the vaporization chamber were at 120° C. and the column was at 65° C.

Detector:
   FID ($H_2$ pressure: 60 kPa, air pressure: 100 kPa)

2. Butene

Gas chromatography:
   gas chromatograph (GC-14B, manufactured by Shimadzu Corporation) with a gas sampler (MGS-4, measuring tube: 1 ml) for Shimadzu gas chromatograph Column:
   packed column Unicarbon A-400, length: 2 m Carrier gas:
   helium (flow rate: 23 ml/min)

Temperature conditions:
   the temperatures of the detector and the vaporization chamber were 120° C. and the column temperature was elevated from 40° C. to 95° C. at a temperature increasing rate of 40° C./min Detector:
   FID ($H_2$ pressure: 70 kPa, air pressure: 100 kPa)

3. Ethylene

Gas chromatography:
   gas chromatograph (GC-14B, manufactured by Shimadzu Corporation) with a gas sampler (MGS-4, measuring tube: 1 ml) for Shimadzu gas chromatograph Column:
   packed column Unibeads 1S, length: 3 m Carrier gas:
   helium (flow rate: 20 ml/min)

Temperature conditions:
   constant temperature conditions where the detector and the vaporization chamber were at 120° C. and the column was at 65° C.

Detector:
   TCD (He pressure: 70 kPa, current: 90 mA, temperature: 120° C.)

Analysis of Collected Solution
   The analysis was performed using the internal standard method, where the analysis solution was prepared by adding 1 ml of 1,4-dioxane as the internal standard to 10 ml of the reaction solution and 0.4 μl of the analysis solution was injected.

Gas chromatography:
   GC-14B, manufactured by Shimadzu Corporation

Column:
   capillary column TC-WAX (length: 30 m, internal diameter: 0.25 mm, film thickness: 0.25 μm)

Carrier gas:
   nitrogen (split ratio: 20, column flow rate: 2 ml/min)

Temperature conditions:
   the temperatures of the detector and the vaporization chamber were both 200° C. and the column was kept at 50° C. for 5 minutes from the initiation of the analysis, thereafter rising to 150° C. at a temperature increasing rate of 20° C./min, and kept at 150° C. for 10 minutes Detector:
   FID ($H_2$ pressure: 70 kPa, air pressure: 100 kPa) Support Support 1:
   natural silica (KA-0, produced by SUD-CHEMIE AG) (specific surface area: 68.5 m²/g, pore volume: 0.71 cm³/g)

Support 2:
   synthetic silica (CARiACT Q-10, produced by Fuji Silicia Kagaku K. K.) (specific surface area: 219.8 m²/g, pore volume: 0.660 cm³/g)

Support 3:
   natural silica (KA-1, produced by SUD-CHEMIE AG) (specific surface area: 113 m²/g, pore volume: 0.64 cm3/g)

Support 4:
   natural silica (KA-160, produced by SUD-CHEMIE AG) (specific surface area: 130 m²/g, pore volume: 0.53 cm³/g)

Support 5:
   synthetic silica (CARiACT Q-6, produced by Fuji Silicia Kagaku K. K.) (specific surface area: 450 m²/g, pore volume: 0.6 cm³/g)

Support 6:
   synthetic silica (CARiACT Q-15, produced by Fuji Silicia Kagaku K. K.) (specific surface area: 200 m²/g, pore volume: 1.0 cm³/g)

Support 7:
   synthetic silica (CARiACT Q-30, produced by Fuji Silicia Kagaku K. K.) (specific surface area: 100 m²/g, pore volume: 1.0 cm³/g)

Support 8:
   synthetic silica (N-602A, produced by Nikki Kagaku K. K.) (specific surface area: 290 m²/g, pore volume: 0.8 cm³/g)

Support 9:
   synthetic silica (N-601A3, produced by Nikki Kagaku K. K.) (specific surface area: 264 m²/g, pore volume: 0.9 cm³/g)

Support 10:
   Synthetic silica (N-602T, produced by Nikki Kagaku K. K.) (specific surface area: 132 m²/g, pore volume: 0.7 cm³/g)

Preparation Process of Catalyst 1

The support 1 was dried for 4 hours in a (hot air) dryer previously adjusted to 110° C. 1 L of the previously dried carrier was subjected to the measurement of the bulk density by a 1 L-volume messcylinder. Tungstophosphoric acid and lithium nitrated were added each to the weight shown in Table 1, 15 ml of pure water was added thereto, and the mixture was uniformly dissolved to obtain a $Li_{0.1}H_{2.9}PW_{12}O_{40}$ aqueous solution (impregnating solution). This impregnating solution was charged into the messcylinder and pure water was added to reach the liquid amount shown in the amount of prepared solution in Table 1 and then uniformly stirred. The previously dried support was weighed to the amount described in Table 1, added to the impregnating solution and thoroughly stirred, thereby impregnating the support. The support impregnated with the solution was air dried for 1 hour and thereafter dried for 5 hours by a hot air dryer adjusted to 150° C. The weight of the catalyst obtained was measured.

Preparation Process of Catalysts 2 to 12

The preparation was performed as described in Preparation Process of Catalyst 1 by changing the kind and weight of the support, the kind and weight of the catalyst component and the weight of lithium nitrate as shown in Table 1. The catalyst was supported on the support in the same manner as in Preparation Process of Catalyst 1.

TABLE 1

| Name of Catalyst | Support | Bulk Density (g/L) | Weight of Support (g) | Kind of Catalyst Component | Amount of Catalyst Component (g) | Amount of Lithium Nitrate (g) | Volume of Prepared Solution (ml) | Dry Weight (g) |
|---|---|---|---|---|---|---|---|---|
| catalyst 1 | 1 | 558 | 55.8 | HPW | 65.33 | 0.1318 | 34 | 113.6 |
| catalyst 2 | 2 | 456 | 45.6 | HSiW | 34.88 | 0.0719 | 43 | 75.6 |
| catalyst 3 | 3 | 573 | 57.3 | HPW | 65.33 | 0.1318 | 33 | 124.5 |
| catalyst 4 | 4 | 575 | 57.5 | HPW | 65.33 | 0.1318 | 32 | 113.8 |
| catalyst 5 | 5 | 627 | 62.7 | HSiW | 34.88 | 0.0719 | 33 | 94.3 |
| catalyst 6 | 6 | 446 | 44.6 | HSiW | 34.88 | 0.0719 | 40 | 75.2 |
| catalyst 7 | 7 | 432 | 43.2 | HSiW | 34.88 | 0.0719 | 41 | 74.5 |
| catalyst 8 | 8 | 811 | 81.1 | HPW | 35.63 | 0.0718 | 64 | 114.7 |
| catalyst 9 | 9 | 703 | 70.3 | HPW | 35.63 | 0.0718 | 83 | 102.9 |
| catalyst 10 | 10 | 813 | 81.3 | HPW | 35.63 | 0.0718 | 69 | 114.3 |
| catalyst 11 | 2 | 456 | 45.6 | HPVW | 35.90 | 0.0753 | 43 | 76.3 |
| catalyst 12 | 2 | 456 | 45.6 | HSiVW | 35.90 | 0.0753 | 43 | 75.9 |

HPW: $H_3PW_{12}O_{40}$
HSiW: $H_4SiW_{12}O_{40}$
HPVW: $H_4PVW_{12}O_{40}$
HSiVW: $H_5SiVW_{12}O_{40}$

EXAMPLE 1

40 ml of the catalyst obtained by Preparation Process of Catalyst 1 was filled in a reaction tube and a mixed gas of ethylene:acetic acid:steam:nitrogen shown in Table 2 was introduced thereinto at a temperature of 165° C. and a pressure of 0.8 MPaG (gauge pressure) to perform the reaction. The results are shown in Table 3.

TABLE 2

| | Catalyst | Starting Material Gas, ethylene:acetic acid: water:nitrogen:substance added (molar ratio) | Substance Added (ppm)*1 | Gas Flow Rate (NL/hr) | Pressure (MPaG) | Reaction Time (hr) | Reaction Temperature (° C.) |
|---|---|---|---|---|---|---|---|
| Example 1 | 1 | 78.5:8.0:4.5:9.0 | none | 60.0 | 0.8 | 5 | 165 |
| | | | | | | 100 | |
| Example 2 | 2 | 78.5:8.0:4.5:9.0 | none | 60.0 | 0.8 | 5 | 165 |
| | | | | | | 99 | |
| Example 3 | 3 | 78.5:8.0:4.5:9.0 | none | 60.0 | 0.8 | 5 | 165 |
| | | | | | | 100 | |
| Example 4 | 4 | 78.5:8.0:4.5:9.0 | none | 60.0 | 0.8 | 5 | 165 |
| | | | | | | 103 | |
| Example 5 | 5 | 78.5:8.0:4.5:9.0 | none | 60.0 | 0.8 | 5 | 165 |
| | | | | | | 98 | |
| Example 6 | 6 | 78.5:8.0:4.5:9.0 | none | 60.0 | 0.8 | 5 | 165 |
| | | | | | | 100 | |
| Example 7 | 7 | 78.5:8.0:4.5:9.0 | none | 60.0 | 0.8 | 5 | 165 |
| | | | | | | 100 | |
| Example 8 | 8 | 78.5:8.0:4.5:9.0 | none | 60.0 | 0.8 | 5 | 165 |
| | | | | | | 100 | |
| Example 9 | 9 | 78.5:8.0:4.5:9.0 | none | 60.0 | 0.8 | 5 | 165 |
| | | | | | | 100 | |
| Example 10 | 10 | 78.5:8.0:4.5:9.0 | none | 60.0 | 0.8 | 5 | 165 |
| | | | | | | 100 | |
| Example 11 | 11 | 78.5:8.0:4.5:9.0 | none | 60.0 | 0.8 | 5 | 165 |
| | | | | | | 100 | |
| Example 12 | 12 | 78.5:8.0:4.5:9.0 | none | 60.0 | 0.8 | 5 | 165 |
| | | | | | | 100 | |
| Comparative Example 1 | 1 | 78.5:8.0:4.5:8.2:0.8 | 1-butene (10088) | 60.5 | 0.8 | 5 | 165 |
| | | | | | | 100 | |
| Comparative Example 2 | 1 | 78.5:8.0:4.5:8.2:0.8 | 2-octene (10088) | 60.5 | 0.8 | 5 | 165 |
| | | | | | | 103 | |

TABLE 2-continued

|  | Catalyst | Starting Material Gas, ethylene:acetic acid: water:nitrogen:substance added (molar ratio) | Substance Added (ppm)*1 | Gas Flow Rate (NL/hr) | Pressure (MPaG) | Reaction Time (hr) | Reaction Temperature (° C.) |
|---|---|---|---|---|---|---|---|
| Comparative Example 3 | 1 | 78.5:8.0:4.5:8.2:0.8 | TMP (10088) | 60.5 | 0.8 | 5 98 | 165 |
| Comparative Example 4 | 2 | 78.5:8.0:4.5:8.2:0.8 | 1-butene (19975) | 60.5 | 0.8 | 5 102 | 165 |
| Comparative Example 5 | 1 | 78.5:8.0:4.5:7.4:1.6 | 2-BA (19975) | 61.0 | 0.8 | 5 105 | 165 |
| Comparative Example 6 | 1 | 78.5:8.0:4.5:8.2:0.8 | 2-BuOH (19975) | 61.0 | 0.8 | 5 98 | 165 |
| Comparative Example 7 | 2 | 78.5:8.0:4.5:7.8:1.2 | 2-BEE (15056) | 60.7 | 0.8 | 5 100 | 165 |

TMP: 2,2,4-trimethylolpentane
2-BEE: 2-butyl ethyl ether
2-BA: 2-butyl acetate
2-BuOH: 2-butyl alcohol
*1: concentration (ppm) when additive/(ethylene + substance added)

TABLE 3

|  | Catalyst | Substance Added (ppm)*1 | STY of Ethyl Acetate (g/L-hr) | Trace By-Products (wt %) |
|---|---|---|---|---|
| Example 1 | 1 | none | 191 | 0.0047 |
|  |  |  | 186 | 0.0123 |
| Example 2 | 2 | none | 252 | 0.0001 |
|  |  |  | 236 | 0.0007 |
| Example 3 | 3 | none | 212 | 0.0004 |
|  |  |  | 204 | 0.0160 |
| Example 4 | 4 | none | 224 | 0.0127 |
|  |  |  | 213 | 0.0234 |
| Example 5 | 5 | none | 268 | 0.0003 |
|  |  |  | 251 | 0.0010 |
| Example 6 | 6 | none | 189 | 0.0003 |
|  |  |  | 180 | 0.0005 |
| Example 7 | 7 | none | 130 | 0.0004 |
|  |  |  | 125 | 0.0008 |
| Example 8 | 8 | none | 178 | 0.0009 |
|  |  |  | 169 | 0.0012 |
| Example 9 | 9 | none | 95 | 0.0006 |
|  |  |  | 90 | 0.0010 |
| Example 10 | 10 | none | 205 | 0.0303 |
|  |  |  | 185 | 0.0011 |
| Example 11 | 11 | none | 148 | 0.0303 |
|  |  |  | 140 | 0.0400 |
| Example 12 | 12 | none | 139 | 0.0160 |
|  |  |  | 131 | 0.0250 |

*1: concentration (ppm) when additive/(ethylene + substance added)

EXAMPLES 2 to 12

The reactions were performed in the same manner as in Example 1 except for changing Catalyst 1 in Example 1 to Catalysts 2 to 12 as shown in Table2. The results are shown in Table 3.

COMPARATIVE EXAMPLES 1, 2, 3, 5, AND 6

The reactions were performed in the same manner as in Example 1 except for changing the reaction gas composition as shown in Table 2. The results are shown in Table 4. As compared with Example 1, the STY of ethyl acetate after about 100 hours seriously decreased, trace by-products increased and a part was separated from the reaction solution and became oily.

TABLE 4

|  | Catalyst | Substance Added (ppm) *1 | STY of Ethyl Acetate (g/L-hr) | Trace By-Products (wt %) |
|---|---|---|---|---|
| Comparative Example 1 | 1 | 1-butene (10088) | 200 166 | 2.4277 5.3126 |
| Comparative Example 2 | 1 | 2-octene (10088) | 66 43 | Oil was produced. Oil was produced. |
| Comparative Example 3 | 1 | TMP (10088) | 197 171 | Oil was produced. Oil was produced. |
| Comparative Example 4 | 2 | 1-butene (19975) | 203 165 | 6.3111 8.2766 |
| Comparative Example 5 | 1 | 2-BA (19975) | 192 153 | 1.9833 3.5211 |
| Comparative Example 6 | 1 | 2-BuOH (19975) | 195 177 | 1.5633 3.0122 |
| Comparative Example 7 | 2 | 2-BEE (15056) | 203 181 | 6.3111 7.2812 |

TMP: 2,2,4-trimethylolpentane
2-BEE: 2-butyl ethyl ether
2-BA: 2-butyl acetate
2-BuOH: 2-butyl alcohol
*1: concentration (ppm) when additive/(ethylene + substance added)

COMPARATIVE EXAMPLES 4 AND 7

The reactions were performed in the same manner as in Example 2 except for changing the reaction gas composition as shown in Table 2. The results are shown in Table 4. As compared with Example 2, the STY of ethyl acetate seriously decreased and trace by-products increased.

EXAMPLE 13

Figure 3:
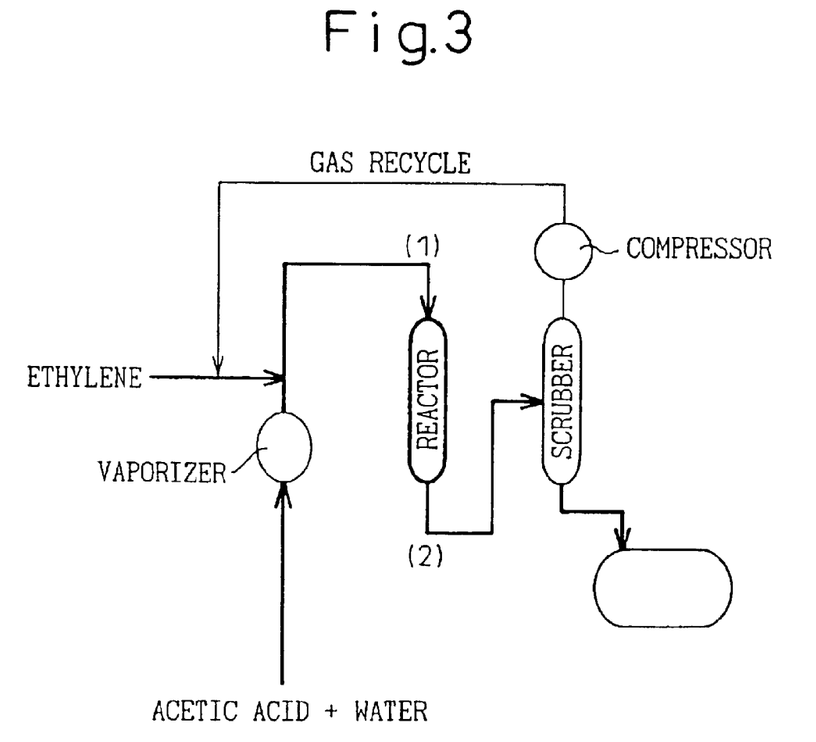
FIG. 3 is a schematic view of a testing apparatus used in the examples.

750 ml of the catalyst shown in Table 5 was filled in a reactor of a reaction apparatus schematically shown in FIG. 3. The conditions were set such that the temperature of the reactor was 160° C., the temperature of the vaporizer was 180° C., the pressure of the entire system was 0.8 MPaG (gauge pressure) and the condensation temperature in the scrubber was −5° C. The amount of ethylene fed in FIG. 3 was 49.0 g/hr and the gas not condensed in the scrubber was recycled by a compressor. Other conditions are shown in Table 5.

TABLE 5

| | Catalyst | Gas Composition in (1) after the reaction for 100 Hours, ethylene:acetic acid:water:nitrogen:ethyl acetate:butene (molar ratio) | Butene Concentration (ppm) | Gas Flow Rate (NL/hr) | Pressure (MPaG) | Temperature of Scrubber (° C.) | Reaction Time (hr) | Reaction Temperature (° C.) | STY of Ethyl Acetate (g/L-hr) | Trace By-Products (wt %) |
|---|---|---|---|---|---|---|---|---|---|---|
| Example 13 | 1 | 78.5:8.0:4.5:8.8:0.2:0.0016 | 20 | 1125 | 0.8 | −5 | 100 | 165 | 181 | 0.0056 |
| | | | | | | | 500 | | 183 | 0.0053 |
| Example 14 | 2 | 78.5:8.0:4.5:8.7:0.2:0.0950 | 1200 | 1125 | 0.8 | 10 | 100 | 165 | 240 | 0.0005 |
| | | | | | | | 500 | | 228 | 0.0010 |
| Example 15 | 1 | 78.5:8.0:4.5:8.5:0.2:0.318 | 4000 | 1125 | 0.8 | 30 | 100 | 165 | 175 | 0.0086 |
| | | | | | | | 500 | | 148 | 0.0090 |
| Comparative Example 9 | 1 | 78.5:8.0:4.5:7.8:0.2:0.953 | 12000 | 1125 | 0.8 | 60 | 100 | 165 | 160 | 5.9030 |
| | | | | | | | 500 | | 73 | 6.3310 |

After starting the feeding of raw materials, the inlet concentration (analysis value at (1) of FIG. 3) was stabilized within 50 hours, therefore, the operation was continued as it is. The reaction results calculated from the inlet concentration and the reaction gas concentration at the outlet (analysis value at (3) of FIG. 3) after 100 hours or 500 hours are shown in Table 5.

EXAMPLES 14 AND 15 AND COMPARATIVE EXAMPLE 8

The reactions were performed in the same manner as in Example 13 except for changing the catalyst, the butene concentration and the temperature in the scrubber to the conditions shown in Table 5.

The reaction results are shown in Table 5.

Industrial Applicability

As described above, in the process for producing an ester from a carboxylic acid and an ethylene in the presence of an acid catalyst, when the concentration of olefin having 3 or more carbon atoms in the raw materials is controlled to 10,000 ppm or less in terms of a molar ratio to the total of the olefin and ethylene or when the concentration of olefin equivalent in the raw materials is controlled to 50,000 ppm or less in terms of a molar ratio to the total of the olefin equivalent and ethylene, a stable operation can be continuously performed for a long period of time.

What is claimed is:

1. A process for producing an ester, comprising reacting a feed of a carboxylic acid and ethylene in the presence of an acid catalyst and in a vapor phase to provide products; and recycling a portion of the products to the feed to form a combined feed and recycle stream; wherein the concentration of olefin selected from the group consisting of trans-2-butene, cis-2-butene and 1-butene in the combined feed and recycle stream is 10,000 ppm or less in terms of the molar ratio to the total of the olefin and ethylene;
   wherein the concentration of the olefin in the combined feed and recycle stream is controlled by removing the olefin from the recycle stream.

2. The process as claimed in claim 1, wherein the concentration of the olefin in the combined feed and recycle stream is 5,000 ppm or less in terms of the molar ratio to the total of the olefin and ethylene.

3. The process as claimed in claim 2, wherein the concentration of the olefin in the combined feed and recycle stream is 1,000 ppm or less in terms of the molar ratio to the total of the olefin and ethylene.

4. A process for producing an ester, comprising reacting a feed of a carboxylic acid and ethylene in the presence of an acid catalyst and in a vapor phase to provide products; and recycling a portion of the products to the feed to form a combined feed and recycle stream; wherein the concentration of olefin equivalent, selected from the group consisting of saturated alcohols having 4 or more carbon atoms, esters of a carboxylic acid and a saturated alcohol having 4 or more carbon atoms, and saturated ethers having 5 or more carbon atoms, which yields trans-2-butene, cis-2-butene or 1-butene, in the combined feed and recycle stream is 50,000 ppm or less in terms of the molar ratio to the total of the olefin equivalent and ethylene;
   wherein the concentration of the olefin in the combined feed and recycle stream is controlled by removing the olefin from the recycle stream.

5. The process as claimed in claim 4, wherein the concentration of the olefin equivalent in the combined feed and recycle stream is 25,000 ppm or less in terms of the molar ratio to the total of the olefin equivalent and ethylene.

6. The process as claimed in claim 5, wherein the concentration of the olefin equivalent in the combined feed and recycle stream is 5,000 ppm or less in terms of the molar ratio to the total of the olefin equivalent and the ethylene.

7. A process for producing an ester, comprising reacting a feed of a carboxylic acid and ethylene in the presence of an acid catalyst and in a vapor phase to provide products; and recycling a portion of the products to the feed to form a combined feed and recycle stream; wherein the sum of the concentration of olefin selected from the group consisting of trans-2-butene, cis-2-butene and 1-butene and one-fifth the concentration of olefin equivalent in the combined feed and recycle stream is 10,000 ppm or less in terms of the molar ratio to the total of the olefin and olefin equivalent and ethylene;
   wherein the concentration of the:olefin in the combined feed and recycle stream is controlled by removing the olefin from the recycle stream.

8. The process as claimed in claim 7, wherein the sum of the concentration of the olefin and one-fifth the concentration of olefin equivalent in the combined feed and recycle stream is 5,000 ppm or less in terms of the molar ratio to the total of the olefin and olefin equivalent and ethylene.

9. The process as claimed claim 8, wherein the sum of the concentration of the olefin and one-fifth the concentration of olefin equivalent in the combined feed and recycle stream is 1,000 ppm or less in terms of the molar ratio to the total of the olefin and olefin equivalent and ethylene.

10. The process as claimed in any one of claims 7 to 9, wherein the olefin equivalent comprises at least one compound selected from the group consisting of saturated alcohols having 3 or more carbon atoms, esters of a carboxylic acid and a saturated alcohol having 3 or more carbon atoms, and saturated ethers having 5 or more carbon atoms.

11. The process as claimed in any one of claims 1 to 3, 4 to 6 and 7 to 9, wherein the carboxylic acid and ethylene is reacted in the presence of water.

12. The process as claimed in any one of claims 1 to 3, 4 to 6 and 7 to 9, wherein the carboxylic acid is at least one of lower aliphatic carboxylic acids having from 1 to 4 carbon atoms.

13. The process as claimed in any one of claims 1 to 3, 4 to 6 and 7 to 9, wherein the acid catalyst comprises at least one compound selected from heteropolyacids and heteropolyacid salts.

14. The process as claimed in claim 13, wherein the heteropolyacid comprises at least one compound selected from the group consisting of silicotungstic acid, phosphotungstic acid, phosphomolybdic acid, silicomolybdic acid, silicovanadotungstic acid, phosphovanadotungstic acid, phosphovanadomolybdic acid, molybdotungstosilicic acid and molybdotungstophosphoric acid.

15. The process as claimed in claim 13, wherein the heteropolyacid salt comprises at least one compound selected from the group consisting of lithium, sodium, potassium, cesium, magnesium, barium, copper, gold, gallium and ammonium salts of heteropolyacids.

16. The process as claimed in claim 10, wherein the carboxylic acid and ethylene is reacted in the presence of water.

17. The process as claimed in claim 10, wherein the carboxylic acid is at least one of lower aliphatic carboxylic acids having from 1 to 4 carbon atoms.

18. The process as claimed in claim 11, wherein the carboxylic acid is at least one of lower aliphatic carboxylic acids having from 1 to 4 carbon atoms.

19. The process as claimed in claim 10, wherein the acid catalyst comprises at least one compound selected from heteropolyacids and heteropolyacid salts.

20. The process as claimed in claim 19, wherein the heteropolyacid comprises at least one compound selected from the group consisting of silicotungstic acid, phosphotungstic acid, phosphomolybdic acid, silicomolybdic acid, silicovanadotungstic acid, phosphovanadotungstic acid, phosphovanadomolybdic acid, molybdotungstosilicic acid and molybdotungstophosphoric acid.

21. The process as claimed in claim 19, wherein the heteropolyacid salt comprises at least one compound selected from the group consisting of lithium, sodium, potassium, cesium, magnesium, barium, copper, gold, gallium and ammonium salts of heteropolyacids.

22. The process as claimed in claim 11, wherein the acid catalyst comprises at least one compound selected from heteropolyacids and heteropolyacid salts.

23. The process as claimed in claim 22, wherein the heteropolyacid comprises at least one compound selected from the group consisting of silicotungstic acid, phosphotungstic acid, phosphomolybdic acid, silicomolybdic acid, silicovanadotungstic acid, phosphovanadotungstic acid, phosphovanadomolybdic acid, molybdotungstosilicic acid and molybdotungstophosphoric acid.

24. The process as claimed in claim 22, wherein the heteropolyacid salt comprises at least one compound selected from the group consisting of lithium, sodium, potassium, cesium, magnesium, barium, copper, gold, gallium and ammonium salts of heteropolyacids.

25. The process as claimed in claim 12, wherein the acid catalyst comprises at least one compound selected from heteropolyacids and heteropolyacid salts.

26. The process as claimed in claim 25, wherein the heteropolyacid comprises at least one compound selected from the group consisting of silicotungstic acid, phosphotungstic acid, phosphomolybdic acid, silicomolybdic acid, silicovanadotungstic acid, phosphovanadotungstic acid, phosphovanadomolybdic acid, molybdotungstosilicic acid and molybdotungstophosphoric acid.

27. The process as claimed in claim 25, wherein the heteropolyacid salt comprises at least one compound selected from the group consisting of lithium, sodium, potassium, cesium, magnesium, barium, copper, gold, gallium and ammonium salts of heteropolyacids.

28. The process as claimed in claim 1, wherein the removal of the olefin from the recycle stream is conducted by solvent absorption, distillation or membrane separation.

29. The process as claimed in claim 4, wherein the removal of the olefin from the recycle stream is conducted by solvent absorption, distillation or membrane separation.

30. The process as claimed in claim 7, wherein the removal of the olefin from the recycle stream is conducted by solvent absorption, distillation or membrane separation.

* * * * *